(12) United States Patent
Austria et al.

(10) Patent No.: US 11,278,310 B2
(45) Date of Patent: Mar. 22, 2022

(54) SAFETY SCALPEL HANDLE

(71) Applicant: Aspen Surgical Products, Inc., Caledonia, MI (US)

(72) Inventors: Georgene Austria, West Hills, CA (US); Justine Pringle, Grand Rapids, MI (US)

(73) Assignee: Aspen Surgical Products, Inc., Caledonia, MI (US)

( * ) Notice: Subject to any disclaimer, the term of this patent is extended or adjusted under 35 U.S.C. 154(b) by 98 days.

(21) Appl. No.: 16/778,008

(22) Filed: Jan. 31, 2020

(65) Prior Publication Data

US 2020/0163690 A1  May 28, 2020

Related U.S. Application Data

(62) Division of application No. 15/463,036, filed on Mar. 20, 2017, now abandoned.

(60) Provisional application No. 62/310,986, filed on Mar. 21, 2016.

(51) Int. Cl.
*A61B 17/3211* (2006.01)
*A61B 17/3213* (2006.01)
*A61B 17/3217* (2006.01)

(52) U.S. Cl.
CPC ...... *A61B 17/3211* (2013.01); *A61B 17/3213* (2013.01); *A61B 17/3217* (2013.01); *A61B 2017/32113* (2013.01)

(58) Field of Classification Search
CPC ...... A61B 2017/32113; A61B 17/3211; A61B 17/3213; A61B 17/3127; B26B 5/00; B26B 5/001; B26B 5/003

USPC .................................................. 30/339, 342
See application file for complete search history.

(56) References Cited

U.S. PATENT DOCUMENTS

| | | | |
|---|---|---|---|
| 334,981 A | 1/1886 | Rampe, Jr. |
| 1,002,468 A | 9/1911 | Strangman |
| D194,087 S | 11/1962 | Jenkins |
| D194,418 S | 1/1963 | Gaspar |
| 3,380,573 A | 4/1968 | Gulotta |

(Continued)

FOREIGN PATENT DOCUMENTS

| AU | 620691 B2 | 2/1992 |
|---|---|---|
| EP | 2915495 A1 | 9/2015 |

(Continued)

OTHER PUBLICATIONS

QlickSmart of Australia, Blade Flask Blade Remover and Blade Cassette, QlickSmart Product Literature, http://qlicksmart.com/English/Home.htm, date unknown, 3 pages.

(Continued)

*Primary Examiner* — Ghassem Alie
*Assistant Examiner* — Samuel A Davies
(74) *Attorney, Agent, or Firm* — Price Heneveld LLP (57) ABSTRACT

A scalpel handle includes a body defining a first end and a channel therein and an insert defining a blade holder disposed at a first end thereof and positionable within the channel of the body with the blade holder extending outwardly away from the first end of the body. A shield is coupled with the body such that the blade holder is positionable within the shield, and a removal wedge is defined on the body, fixed with respect to the shield, and disposed in a substantially fixed lateral position at least partially aligned with a portion of the blade holder.

16 Claims, 11 Drawing Sheets

(56) References Cited

U.S. PATENT DOCUMENTS

| | | |
|---|---|---|
| 3,442,378 A | 5/1969 | Wolfe |
| 3,696,920 A | 10/1972 | Lahay |
| 3,785,544 A | 1/1974 | Smith |
| D231,714 S | 5/1974 | Arthur |
| 3,916,448 A | 11/1975 | Hamel |
| 3,921,289 A | 11/1975 | Hasegawa |
| D248,871 S | 8/1978 | Forsman et al. |
| 4,106,620 A | 8/1978 | Brimmer et al. |
| D249,362 S | 9/1978 | Forsman et al. |
| 4,120,397 A | 10/1978 | Neumann |
| 4,168,777 A | 9/1979 | Gaskell et al. |
| 4,173,071 A | 11/1979 | Ishida |
| 4,180,162 A | 12/1979 | Magney |
| 4,270,416 A | 6/1981 | Thompson |
| 4,318,473 A | 3/1982 | Sandel |
| 4,386,457 A | 6/1983 | Coombs |
| 4,395,807 A | 8/1983 | Eldridge, Jr. et al. |
| D273,615 S | 4/1984 | Maskrey |
| 4,466,539 A | 8/1984 | Frauenhoffer |
| D275,833 S | 10/1984 | Malpass |
| D276,462 S | 11/1984 | Villarreal |
| 4,730,376 A | 3/1988 | Yamada |
| 4,746,016 A | 5/1988 | Pollak et al. |
| 4,903,390 A | 2/1990 | Vidal et al. |
| 4,922,614 A * | 5/1990 | Machida ............ A61B 17/3213 30/339 |
| 4,930,234 A | 6/1990 | Schmidt |
| 4,971,271 A | 11/1990 | Sularz |
| 4,998,334 A | 3/1991 | Pemberton et al. |
| 5,024,326 A | 6/1991 | Sandel et al. |
| 5,036,866 A | 8/1991 | Eldridge, Jr. et al. |
| D319,873 S | 9/1991 | Rouse |
| 5,071,426 A | 12/1991 | Dolgin et al. |
| 5,088,173 A | 2/1992 | Kromer et al. |
| D327,743 S | 7/1992 | Frenkel et al. |
| D328,026 S | 7/1992 | Stenstrom |
| 5,163,553 A | 11/1992 | Cantwell et al. |
| 5,193,678 A | 3/1993 | Janocik et al. |
| D334,973 S | 4/1993 | Valentine et al. |
| 5,207,696 A | 5/1993 | Matwijcow |
| D337,830 S | 7/1993 | Coyne et al. |
| D341,883 S | 11/1993 | Jones et al. |
| D343,687 S | 1/1994 | Houghton et al. |
| 5,275,606 A | 1/1994 | Abidin et al. |
| 5,299,357 A | 4/1994 | Wonderley et al. |
| 5,312,429 A | 5/1994 | Noack |
| 5,330,492 A | 7/1994 | Haugen |
| 5,330,494 A | 7/1994 | Van Der Westhuizen et al. |
| D349,204 S | 8/1994 | Lefebvre |
| 5,346,677 A | 9/1994 | Risk |
| 5,361,902 A | 11/1994 | Abidin et al. |
| 5,363,958 A | 11/1994 | Horan |
| 5,370,654 A | 12/1994 | Abidin et al. |
| D355,513 S | 2/1995 | Posenauer |
| 5,417,704 A | 5/1995 | Wonderley |
| 5,431,672 A | 7/1995 | Cote et al. |
| 5,433,321 A | 7/1995 | Abidin et al. |
| 5,449,068 A | 9/1995 | Gharibian |
| D366,527 S | 1/1996 | Paterson |
| 5,482,067 A | 1/1996 | Wittrock et al. |
| 5,496,340 A | 3/1996 | Adibin |
| D369,295 S | 4/1996 | Kobari et al. |
| 5,527,329 A | 6/1996 | Gharibian |
| D372,782 S | 8/1996 | Spehalski |
| D374,282 S | 10/1996 | Hoftman |
| 5,569,281 A | 10/1996 | Abidin et al. |
| 5,571,127 A | 11/1996 | Decampli |
| D376,647 S | 12/1996 | Marsh et al. |
| D378,408 S | 3/1997 | Pyeatt et al. |
| 5,662,221 A | 9/1997 | Abidin et al. |
| 5,662,669 A | 9/1997 | Abidin et al. |
| 5,667,067 A | 9/1997 | Gabriel |
| 5,683,407 A | 11/1997 | Jolly |
| D387,177 S | 12/1997 | Davis |
| 5,699,908 A | 12/1997 | Frye et al. |
| 5,706,942 A | 1/1998 | Vila et al. |
| 5,729,879 A | 3/1998 | Hoftman |
| 5,741,289 A | 4/1998 | Jolly et al. |
| 5,752,968 A | 5/1998 | Jolly et al. |
| 5,765,470 A | 6/1998 | Sitro |
| 5,791,472 A | 8/1998 | Davis |
| 5,792,162 A | 8/1998 | Jolly et al. |
| 5,827,309 A | 10/1998 | Jolly et al. |
| D402,767 S | 12/1998 | Davis et al. |
| 5,868,771 A | 2/1999 | Newman et al. |
| 5,875,532 A | 3/1999 | Musgrave et al. |
| 5,875,533 A | 3/1999 | Henry |
| 5,938,027 A | 8/1999 | Soroff et al. |
| 5,938,676 A | 8/1999 | Cohn et al. |
| 5,941,892 A | 8/1999 | Cohn et al. |
| 5,964,161 A | 10/1999 | Conway |
| 5,968,663 A | 10/1999 | Muggli |
| 6,212,803 B1 | 4/2001 | Key |
| 6,216,868 B1 | 4/2001 | Rastegar et al. |
| D441,192 S | 5/2001 | Park |
| 6,254,621 B1 | 7/2001 | Shackelford et al. |
| D449,685 S | 10/2001 | Morrison |
| D450,130 S | 11/2001 | Goldstein |
| D450,391 S | 11/2001 | Hunt et al. |
| 6,426,041 B1 | 7/2002 | Smith |
| 6,589,258 B2 | 7/2003 | Pilo et al. |
| D479,328 S | 9/2003 | Reynolds et al. |
| 6,626,925 B2 | 9/2003 | Newman et al. |
| D481,129 S | 10/2003 | Dicesare et al. |
| 6,629,985 B1 | 10/2003 | Kiehne |
| D482,788 S | 11/2003 | Montgomery et al. |
| 6,645,216 B2 | 11/2003 | Masury et al. |
| D483,123 S | 12/2003 | Montgomery et al. |
| D489,454 S | 5/2004 | Koseki |
| D490,153 S | 5/2004 | Montgomery et al. |
| 6,757,977 B2 | 7/2004 | Dambal et al. |
| D504,175 S | 4/2005 | Westbrook |
| 6,955,002 B2 | 10/2005 | Sandel et al. |
| 7,036,660 B1 | 5/2006 | Abidin et al. |
| 7,070,051 B2 | 7/2006 | Kanner et al. |
| D528,206 S | 9/2006 | Bierman |
| D535,026 S | 1/2007 | Griffin et al. |
| 7,155,795 B2 | 1/2007 | Abidin et al. |
| 7,156,231 B1 | 1/2007 | Austria |
| 7,159,713 B1 | 1/2007 | Austria |
| 7,172,611 B2 | 2/2007 | Harding et al. |
| 7,207,999 B2 | 4/2007 | Griffin et al. |
| D542,415 S | 5/2007 | Sandel |
| D544,600 S | 6/2007 | Wentling |
| D549,327 S | 8/2007 | Aparici et al. |
| 7,303,568 B2 | 12/2007 | Jannot |
| D561,898 S | 2/2008 | Goto |
| 7,346,989 B2 | 3/2008 | Shi |
| D568,475 S | 5/2008 | Sandel et al. |
| D568,491 S | 5/2008 | Koseki |
| D568,492 S | 5/2008 | Koseki |
| D568,493 S | 5/2008 | Koseki |
| 7,398,880 B2 | 7/2008 | Henry |
| 7,441,655 B1 | 10/2008 | Hoftman |
| D583,821 S | 12/2008 | Richter |
| 7,458,177 B2 | 12/2008 | Sandel et al. |
| D596,311 S | 7/2009 | Antons |
| D608,015 S | 1/2010 | Sandel |
| D608,456 S | 1/2010 | Sandel |
| D612,050 S | 3/2010 | Baynham |
| D616,089 S | 5/2010 | Van Der Stappen |
| 7,713,280 B2 | 5/2010 | Marshall et al. |
| D618,821 S | 6/2010 | Larsen |
| D621,502 S | 8/2010 | Downs |
| D630,317 S | 1/2011 | Wung |
| D636,894 S | 4/2011 | Tomes et al. |
| D638,137 S | 5/2011 | Gross et al. |
| D638,940 S | 5/2011 | Palmer et al. |
| RE42,507 E | 6/2011 | Wilkinson et al. |
| D648,852 S | 11/2011 | Shi |
| D650,912 S | 12/2011 | Tomes et al. |
| 8,074,364 B2 * | 12/2011 | Nakamura ......... A61B 17/3213 30/335 |
| 8,114,103 B2 | 2/2012 | Rasco |

(56) References Cited

U.S. PATENT DOCUMENTS

| | | |
|---|---|---|
| 8,156,653 B2 | 4/2012 | Austria |
| 8,205,340 B2 | 6/2012 | Austria et al. |
| D662,989 S | 7/2012 | Vulgamott et al. |
| D676,146 S | 2/2013 | Austria |
| D676,573 S | 2/2013 | Austria |
| 8,372,503 B2 | 2/2013 | Austria et al. |
| D683,407 S | 5/2013 | Austria |
| D683,452 S | 5/2013 | Davies et al. |
| D703,626 S | 4/2014 | Hermansen |
| D710,497 S | 8/2014 | Pham et al. |
| D712,062 S | 8/2014 | Austria |
| D712,063 S | 8/2014 | Austria |
| D712,064 S | 8/2014 | Austria |
| D713,958 S | 9/2014 | Srinivasan et al. |
| 8,898,910 B2 | 12/2014 | Ichiyanagi et al. |
| 8,931,181 B2 | 1/2015 | Milton et al. |
| 9,113,946 B2 | 8/2015 | Hajgato et al. |
| 2004/0186496 A1 | 9/2004 | Sandel et al. |
| 2004/0243161 A1 | 12/2004 | Kanodia et al. |
| 2005/0065541 A1 | 3/2005 | Abidin et al. |
| 2005/0204932 A1 | 9/2005 | Tingley |
| 2005/0223640 A1 | 10/2005 | Hall et al. |
| 2006/0027104 A1 | 2/2006 | Perez, Jr. |
| 2006/0041267 A1 | 2/2006 | Henry |
| 2006/0100650 A1 | 5/2006 | Kiehne |
| 2006/0212058 A1 | 9/2006 | Djordjevic et al. |
| 2007/0039844 A1 | 2/2007 | Zyzelewski et al. |
| 2007/0039845 A1 | 2/2007 | Kaforey et al. |
| 2007/0060931 A1 | 3/2007 | Rasco |
| 2007/0255298 A1 | 4/2007 | Djordjevic et al. |
| 2007/0265651 A1 | 11/2007 | Yi et al. |
| 2008/0173187 A1 | 7/2008 | Baker |
| 2008/0272023 A1 | 11/2008 | McCormick et al. |
| 2009/0157110 A1* | 6/2009 | Muto ............. A61B 17/3211 606/167 |
| 2009/0192538 A1 | 7/2009 | Sandel et al. |
| 2009/0267717 A1 | 10/2009 | Baskett |
| 2010/0063522 A1 | 3/2010 | Reaux |
| 2010/0137894 A1 | 6/2010 | Ueno et al. |
| 2010/0168773 A1* | 7/2010 | Funderburk ....... A61B 17/3213 606/167 |
| 2010/0228274 A1 | 9/2010 | Baid |
| 2010/0268258 A1 | 10/2010 | Maxwell |
| 2012/0245610 A1 | 9/2012 | Hajgato et al. |
| 2012/0311869 A1 | 12/2012 | Ichiyanagi et al. |
| 2013/0079804 A1 | 3/2013 | Milton et al. |
| 2013/0245656 A1 | 9/2013 | Austria |
| 2014/0182140 A1* | 7/2014 | Rosenhan .......... A61B 17/3213 30/162 |
| 2015/0201957 A1 | 7/2015 | Shi |
| 2015/0250492 A1 | 9/2015 | Austria |
| 2016/0095614 A1 | 4/2016 | Austria |

FOREIGN PATENT DOCUMENTS

| | | |
|---|---|---|
| GB | 846877 A | 8/1960 |
| GB | 2464751 A | 5/2010 |
| JP | 3026909 B2 | 3/2000 |
| JP | 3126664 B2 | 1/2001 |
| JP | 2002177291 A | 6/2002 |
| JP | 2006340857 A | 12/2006 |
| JP | 5390694 B2 | 1/2014 |
| WO | 9424020 A1 | 10/1994 |
| WO | 2008132762 A1 | 11/2008 |
| WO | 2011108099 A1 | 9/2011 |
| WO | 2012002910 A1 | 1/2012 |

OTHER PUBLICATIONS

Smeak, Daniel et al., Core Surgical Skills: Basic Instrument Use, Texas A&M University School of Veterinary medicine and Biomedical Sciences, 2011, pp. 1-9.

Swann-Morton, Surgical Blade removal by Swann-Morton, date unknown, 2 pages.

Trademark Medical, Personal Protective Equipment & Sharps Safety Products: Scalpel Safety, 2010, 2 pages.

The Official Journal of the Anethesia Patient Safety Foundation, APSF Hosts Medication Safety Conference, vol. 25, No. 1, 1-20, 2010, 7 pages.

ADV Medical, Needle Counters Selection, date unknown, 2 pages.

Southmedic, Introducing . . . the only safety scalpel that fits your favorite handle, Safety Cabo, date unkown, 2 pages.

Tyco Healthcare Group LP, DEVON* Needle Counters, 2003, 2 pages.

Xodus Medical, Needle Counter and Sharps Disposal Systems, date unknown, 4 pages.

* cited by examiner

SAFETY SCALPEL HANDLE

CROSS-REFERENCE TO RELATED APPLICATION

This application is a divisional of U.S. patent application Ser. No. 15/463,036, entitled "SAFETY SCALPEL HANDLE," filed on Mar. 20, 2017, now abandoned, which claims the benefit of U.S. Provisional Application No. 62/310,986 filed on Mar. 21, 2016, entitled, "SAFETY SCALPEL HANDLE," the entire contents of which are incorporated herein by reference.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be revisited.

TECHNOLOGICAL FIELD

The present disclosure relates generally to a scalpel handle. In particular, the scalpel handle can retain a scalpel blade in an assembly that includes a safety sheath and a release mechanism to allow for removal of the blade.

BACKGROUND

Accidental cuts or punctures may occur by way of sharp instruments, either during use, during transfer from one person to another, or from inadvertent misplacement thereof in certain locations. Such injuries are particularly impactful in the medical arena, as diseases can be spread through accidental contact with "sharps," including scalpel blades or the like. In particular, scalpels may include a handle that can be assembled with a disposable blade. Such handles may also be disposable or may be reusable (such as by being made of a material that can be sterilized using an autoclave of the like). Further, many such handles may not include any protection from contact with the blade when being assembled thereto and, further, may present additional opportunity for injury during removal of a to-be-disposed blade prior to reuse or disposal of the handle.

Accordingly, further advances in protection from injury due to inadvertent contact with scalpel blades, including during removal, are desired.

SUMMARY

According to one aspect of the present disclosure, a scalpel handle includes a body defining a first end and a channel therein and an insert defining a blade holder disposed at a first end thereof and positionable within the channel of the body with the blade holder extending outwardly away from the first end of the body. A shield is coupled with the body such that the blade holder is positionable within the shield, and a removal wedge is defined on the body, fixed with respect to the shield, and disposed in a substantially fixed lateral position at least partially aligned with a portion of the blade holder.

According to another aspect of the present disclosure, a scalpel handle includes a body defining a channel extending in a longitudinal direction along a side thereof and having a shield portion disposed at a first end thereof that at least partially encloses the channel, a removal ramp defined along a portion of the channel adjacent the shield. The scalpel handle further includes an insert slidably disposed within the channel between a fully-extended position and a removal position with an intermediate extended position and a retracted position therebetween and having a blade holder defined on a first end thereof that passes the first end of the body during movement of the insert from the intermediate extended position to the retracted position and passes the removal ramp during movement of the insert into the removal position.

According to another aspect of the present disclosure, a scalpel handle includes a body defining a channel extending in a longitudinal direction along a side thereof and having a shield portion disposed at a first end thereof that at least partially encloses the channel, a removal ramp defined along a portion of the channel adjacent the shield. The scalpel handle further includes an insert having a blade holder defined on a first end thereof, the blade holder being configured for removably retaining a scalpel blade on the insert. The insert is slidably disposed within the channel between a retracted position and a removal position such that the blade holder, when retaining a scalpel blade thereon, moves from remote from the removal ramp to proximate the removal ramp, thereby brining the scalpel blade into contact with the removal ramp and disengaging the scalpel blade from the blade holder.

These and other features, advantages, and objects of the present device will be further understood and appreciated by those skilled in the art upon studying the following specification, claims, and appended drawings.

DETAILED DESCRIPTION OF EMBODIMENTS

Figures 1, 2:
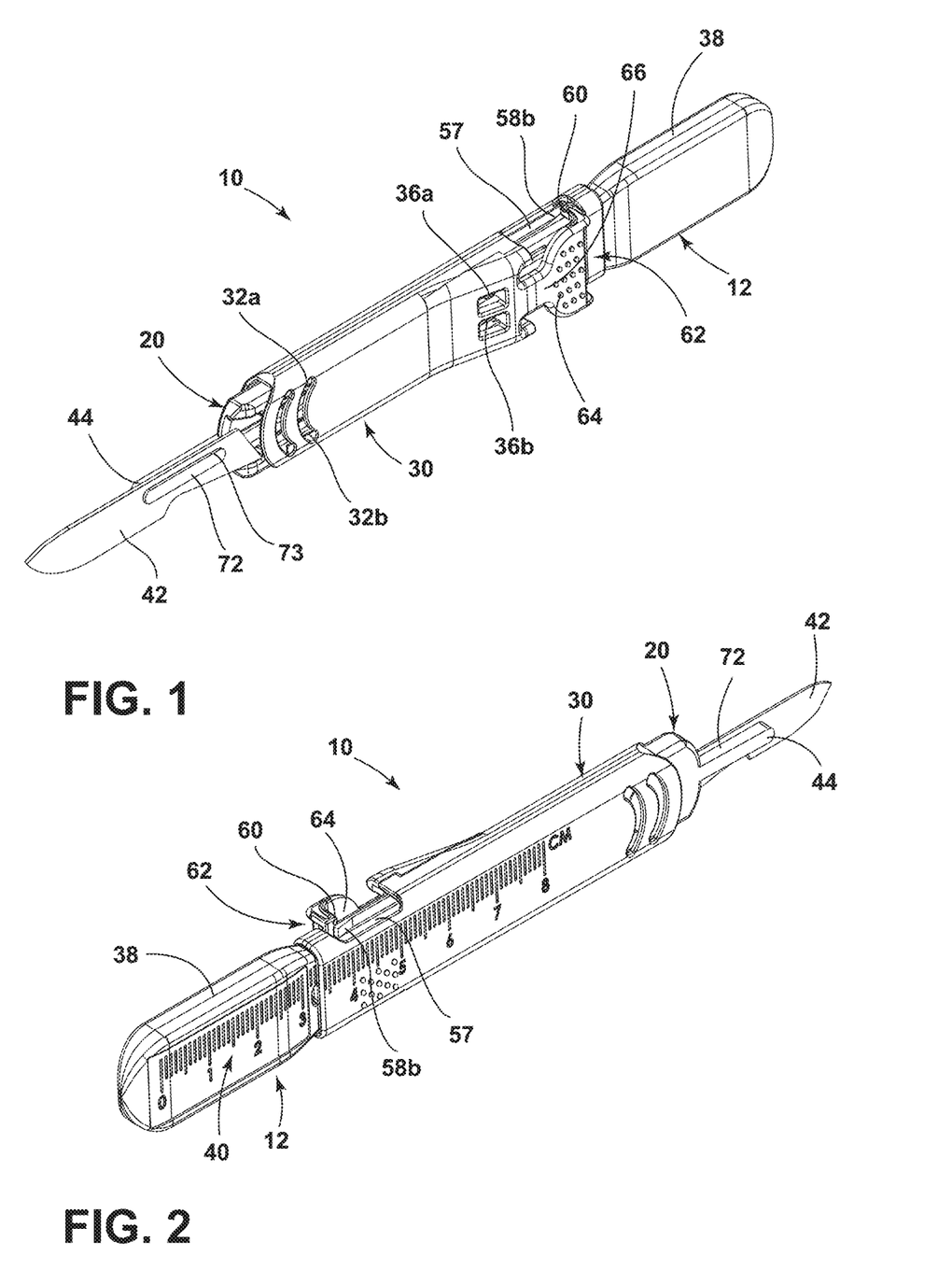
FIG. 1 is a front perspective view of a scalpel handle with a shield thereof in a retracted position and assembled with a blade.
FIG. 2 is a rear perspective view of the scalpel handle assembly of FIG. 1.

For purposes of description herein the terms "upper," "lower," "right," "left," "rear," "front," "vertical," "horizontal," and derivatives thereof shall relate to the device as oriented in FIG. 1. However, it is to be understood that the device may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Referring to the embodiment illustrated in FIG. 1, reference numeral 10 generally designates a scalpel handle assembly, which may simply be referred to as a "handle." The scalpel handle 10 includes a body 12 defining at least one channel 32a,32b extending in a longitudinal direction 76 along a side thereof and a blade holder 44 disposed at a first end 20 thereof and a shield 30 coupled with the body 12. The shield 30 is slideable along the body 12 between a retracted position and a removal position with an intermediate extended position therebetween. The shield 30 defines a removal flange 36a,36b extending within an interior of the shield 30 and slideably disposed within the channel 32a,32b to pass the first end 20 of the body 12 during movement of the shield 30 from the extended position to the removal position.

Figure 3:
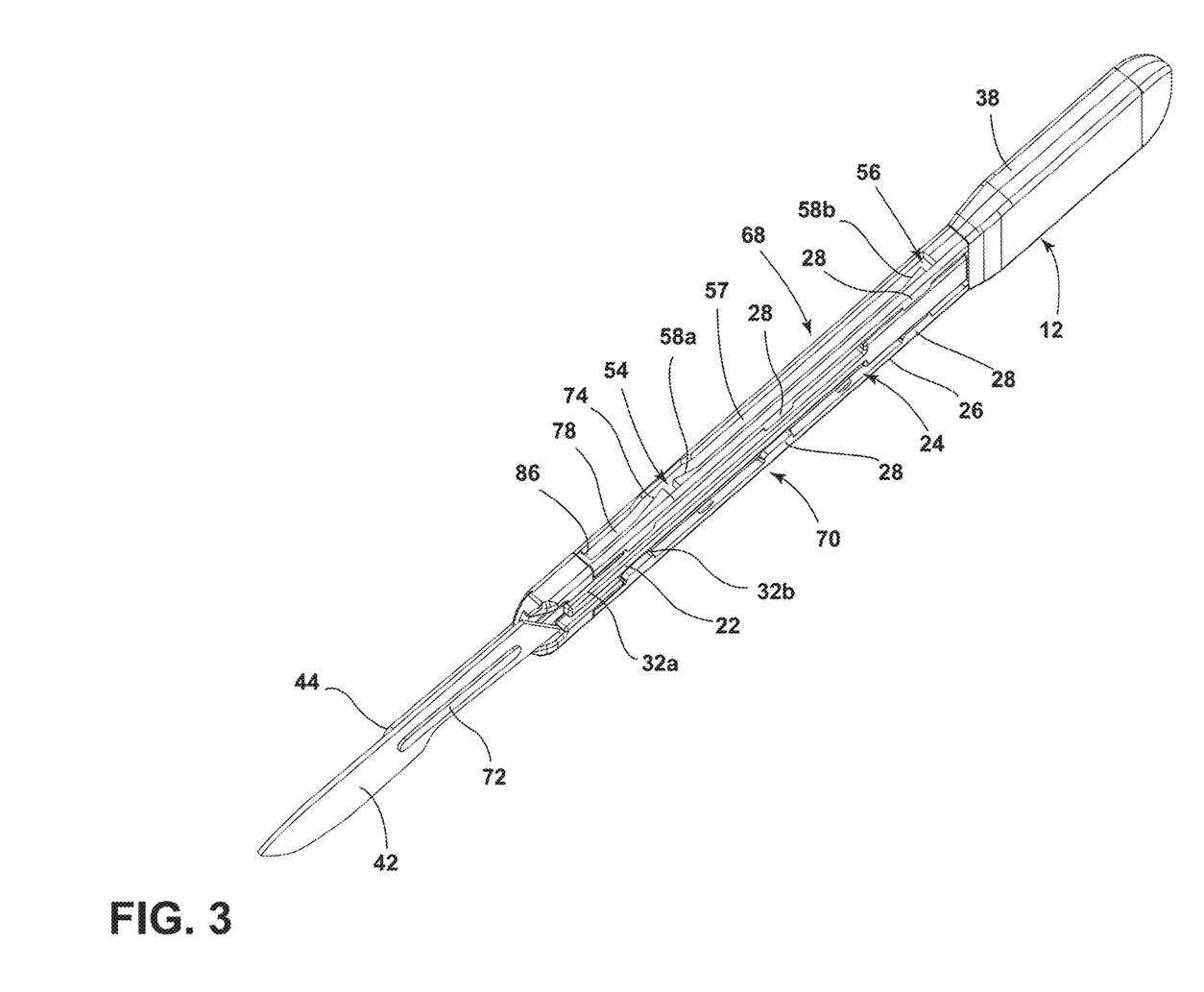
FIG. 3 is a front perspective view of a body of the scalpel handle assembly of FIG. 1.
Figure 4:
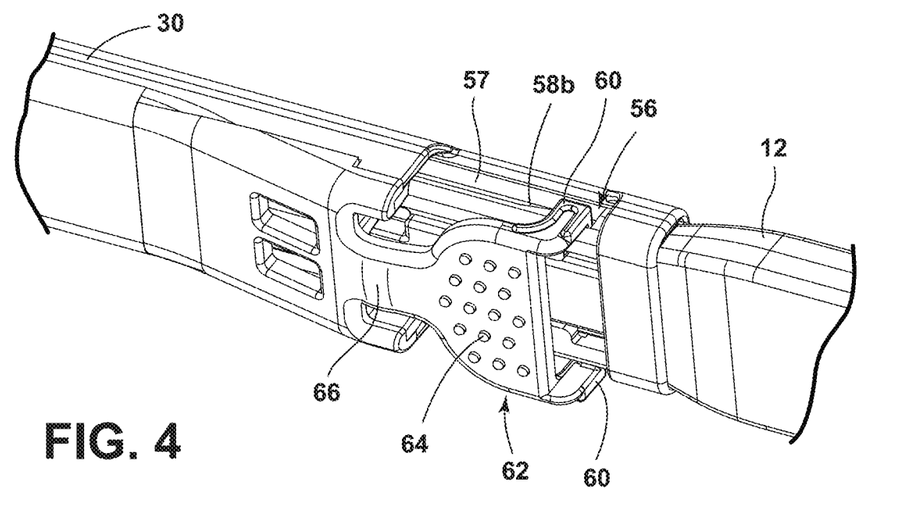
FIG. 4 is a perspective detail view of a locking mechanism of the scalpel handle of FIG. 1.
Figure 5:
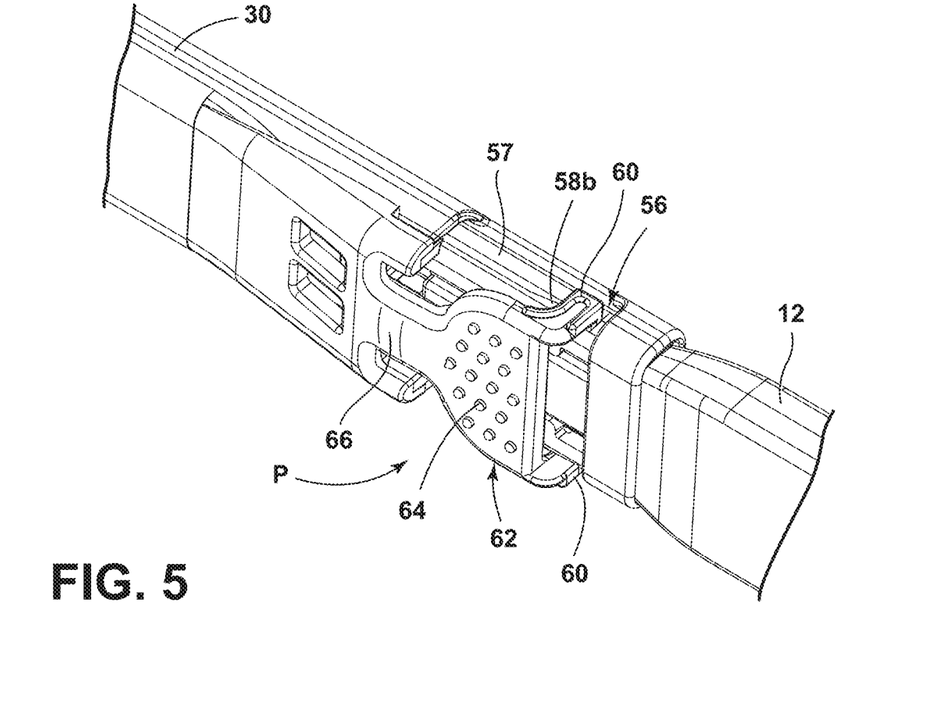
FIG. 5 is a perspective detail view of the locking mechanism of FIG. 4 in a depressed position.

As shown in FIGS. 1 and 2, the handle 10 according to the embodiment of FIGS. 1-12 may include an insert 22 as a portion thereof. The insert 22 includes blade holder 44 on an end thereof and extending outward beyond first end 20 of body 12 to retain a blade 42 thereon that may be thereby removeably coupled with handle 10. The insert 22 can be coupled with the body 12 such as by being retained within a cavity 24 having an open side 26 along a portion of body 12. Insert 22 can be retained within cavity 24 by a plurality of retention tabs 28 (FIG. 3) and/or can be secured in place using adhesives or the like. In an example, a handle 10 according to such a construction can be a disposable handle 10, wherein body 12 comprises a plastic material or the like that, while not amenable to common sterilization processes, can be manufactured at a cost that generally permits a one-time (or single procedure) use. The use of insert 22 within body 12 can provide a greater weight for handle 10, which some may find to be more comfortable or precise feel. Further, the incorporation of the blade holder 44 as an integral portion of insert 22 can provide a more rigid coupling with and retention of blade 42 on handle 10. As shown in FIG. 3, insert 22 defines a plurality of channels 32a,32b therein that can accommodate portions of removal flanges 36a,36b respectively therein to allow removal flanges 36a,36b to move along handle 10 along with shield 30, without interference therebetween, as discussed further below.

Figure 6:
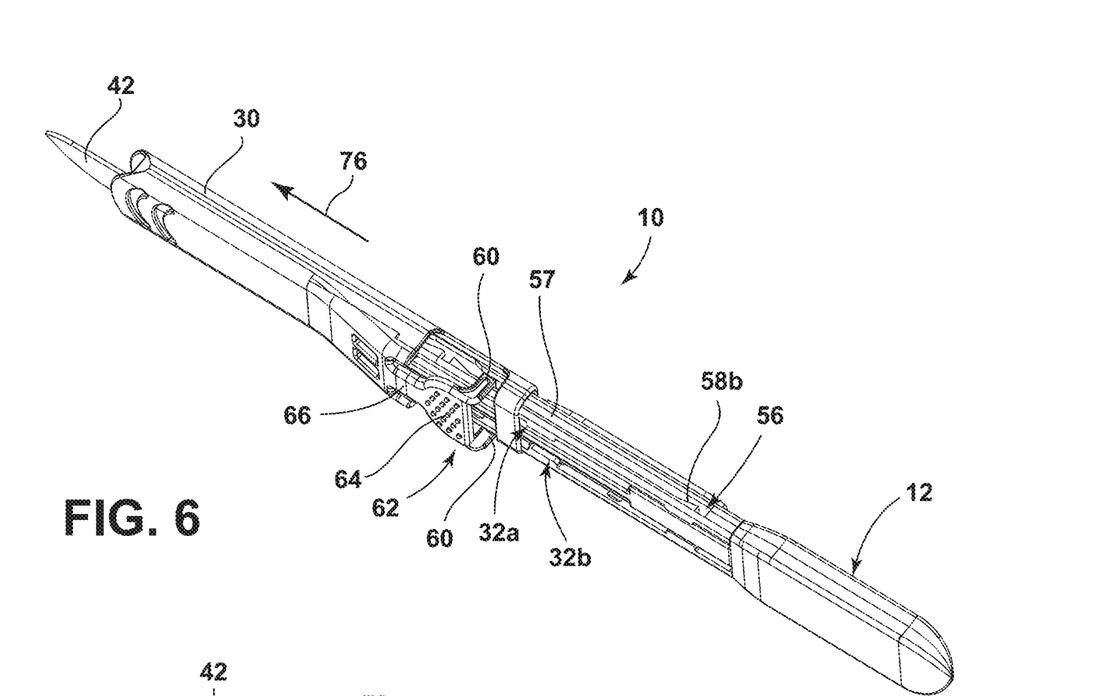
FIG. 6 is a rear perspective view of the scalpel handle assembly of FIG. 1 during movement of the shield into an extended position.
Figure 7:
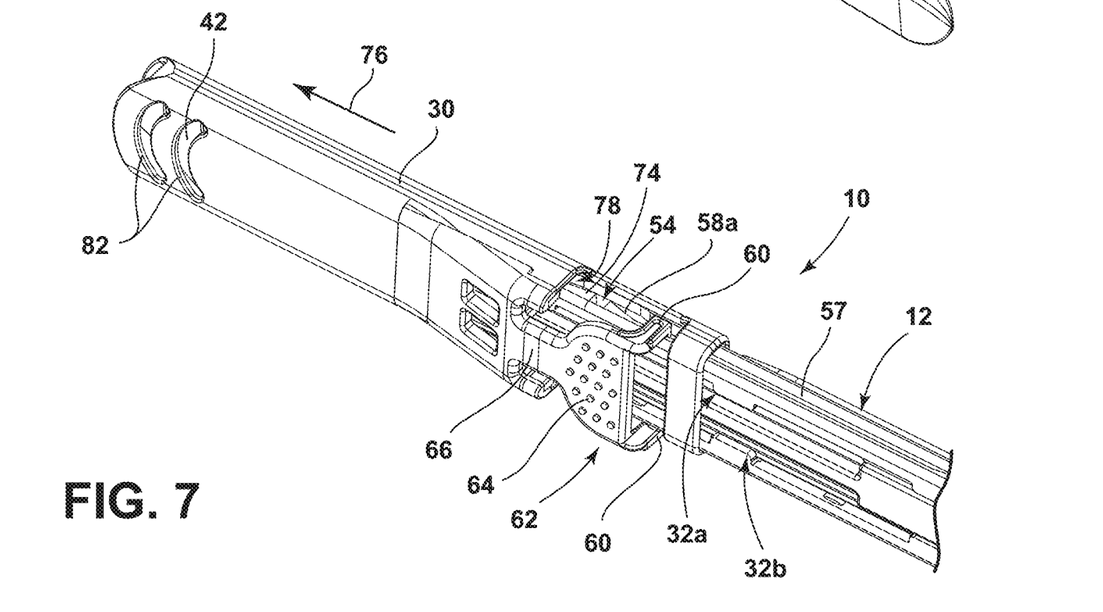
FIG. 7 is a rear perspective view of the scalpel handle assembly of FIG. 1 with the shield in the extended position.
Figure 8:
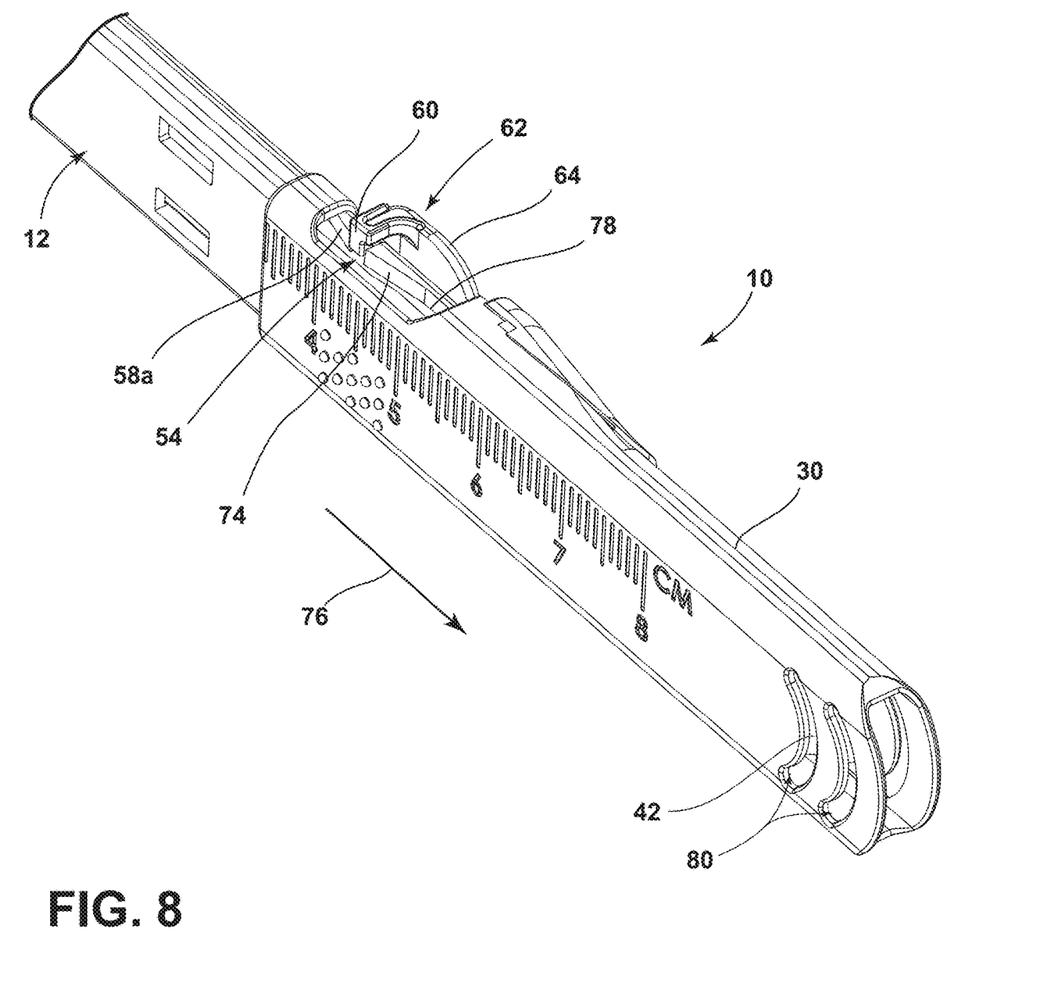
FIG. 8 is a front perspective detail view of the scalpel handle assembly of FIG. 7.

As shown in FIGS. 3-8, body 12 of handle 10 includes tracks 57 that have first 54 and second 56 locking channels, with both locking channels 54 and 56 being connected by a portion of track 57 having elevated ramps 58 adjacent to locking channels 54 and 56. Track 57 and locking channels 54 and 56 engage with tabs 60 of a locking mechanism 62 on shield 30. When the shield 30 is directed towards either the first locking channel 54 or the second locking channel 56, tabs 60 ride over ramps 58, thereby causing inward flexing of locking mechanism 62 by bending of flexible portion 66 thereof (locking mechanism 62 being configured as a cantilevered section integral with shield 30) until tabs 60 snap into either first locking 54 or second locking channel 56, causing an audible signal and a tactual feel indicating that the shield 30 is positively locked in either the retracted position (when locking mechanism 62 is engaged with second locking channel 56) or the extended position (when locking mechanism 62 is engaged with first locking channel 54). It is noted that a set of locking channels 54 and 56 is shown connected by a track 57 on a top surface 68 of body 12, and that a corresponding (or substantially identical) set of locking channels connected by a corresponding (or substantially identical) track can be present on bottom surface 70 of body 12 as well. When shield 30 is locked in either the extended position, as shown in FIG. 8, or the retracted position, as shown in FIG. 1, the locking mechanism 60 may be released by depressing button 64 inward in direction P, shown in FIG. 5, and beginning movement of shield 30 out of such position (such as in direction 76, shown in FIG. 6). The locking mechanism 62 is released when tabs 60 travel beyond the respective locking channels 54 or 56, allowing the shield 30 to be moved either forward or backward, as shown, for example in FIG. 5, which shows inward movement of button 64 in direction P to allow tab 60 to move out of the locking channel 56 associated with the retracted position (FIG. 1).

Handle 10 is configured such that the blade 42 can be coupled with the blade tang 72 of blade holder 44 when the shield 30 is in the retracted position. Such coupling can be done according to generally standard blade loading technique and can include assembly of a slot 45 within blade 42 into a mounting groove 73 (FIG. 1) within blade tang 72. As shown in FIG. 1, blade holder 44 of handle 10 is exposed when shield 30 is in the retracted position such that blade 42 can be assembled on the handle 10 when shield 30 is retracted.

Figure 9:
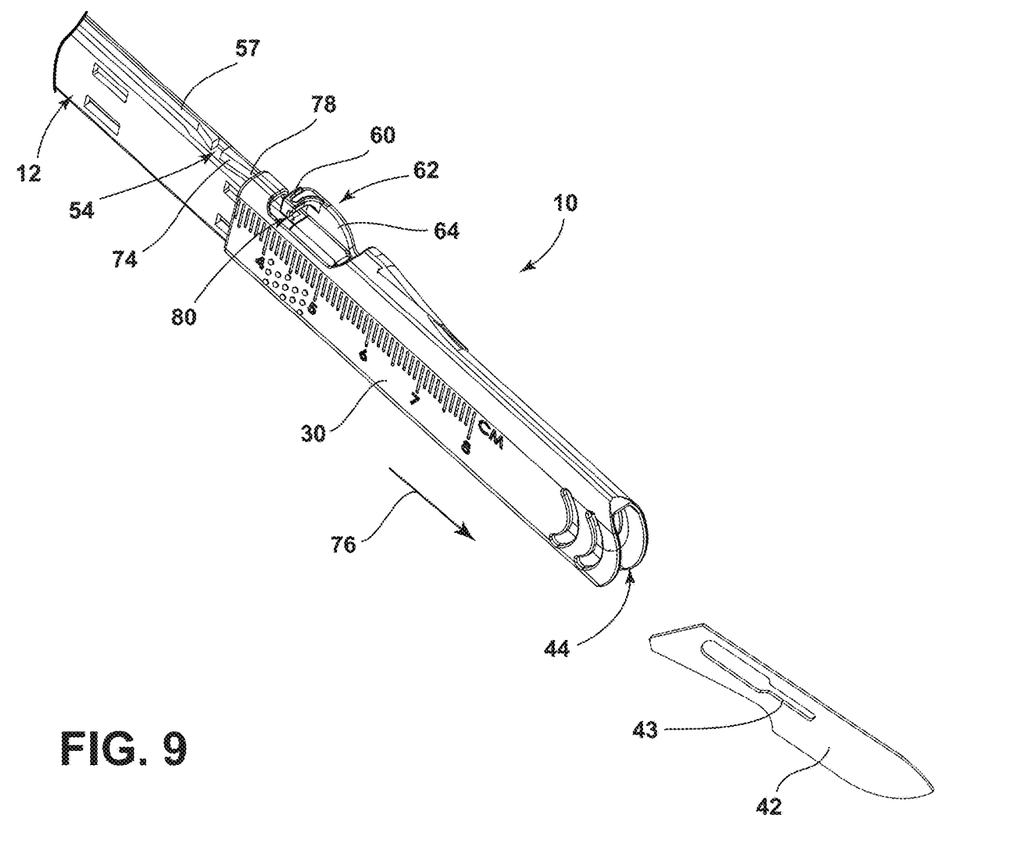
FIG. 9 is a front perspective detail view of the scalpel handle assembly of FIG. 1 with the shield moved into a blade removal position.

Handle 10 includes features arranged to facilitate an "automatic" blade removal. Handle 10 is further configured such that this blade 42 removal is only achieved when the shield 30 is moved forward from the extended position (FIG. 8) toward the removal position shown in FIG. 9. This is achieved when handle 10 is initially in the extended position (FIG. 8) with tab 60 engaged with first locking channel 54 by pressing the button 64 of locking mechanism 62 inward (generally in direction P, as discussed above) and pushing the shield 30 forward over an additional ramp 74 and into an extension portion 78 of track 57 (of which similar portions may be included in a similar track on bottom side 70 of body 12). Such movement results in the removal flanges 36a, 36b that extend inward within shield 30 to push the blade 42 in direction 76 to completely remove the blade 42 from blade holder 44 of the handle 10, as shown in FIG. 9.

As discussed above, removal flanges 36a, 36b extend inward within shield 30 and are recessed with respect to body 12 by extending into respective channels 32 within handle 10 (such as within insert 22 in the present embodiment). Channels 32 extend longitudinally along body 12, again, such that removal flanges 36a, 36b, while recessed within body 12, can move freely in direction 76 along body 12 with movement of shield 30, as discussed above. The recessed arrangement of removal flanges 36a, 36b allows at least portions thereof to extend laterally past the trailing edge 84 of blade 42 to align with a portion of the blade holder 44 and/or with mounting groove 73. As illustrated in FIG. 11, this positioning allows for at least one of removal flanges 36a, 36b to be positioned around or generally laterally behind trailing end 84 of blade 42 when shield 30 is moved out of the extended position and in direction 76 toward the removal position. As further shown in FIGS. 10A, 10B, ad 10C, this arrangement allows for engagement of at least one of the removal flanges 36a, 36b (depending, for example, on the particular geometry blade 42) to contact trailing edge 84 of blade 42 and to implement removal of blade 42 from blade holder 44.

Figure 10A:
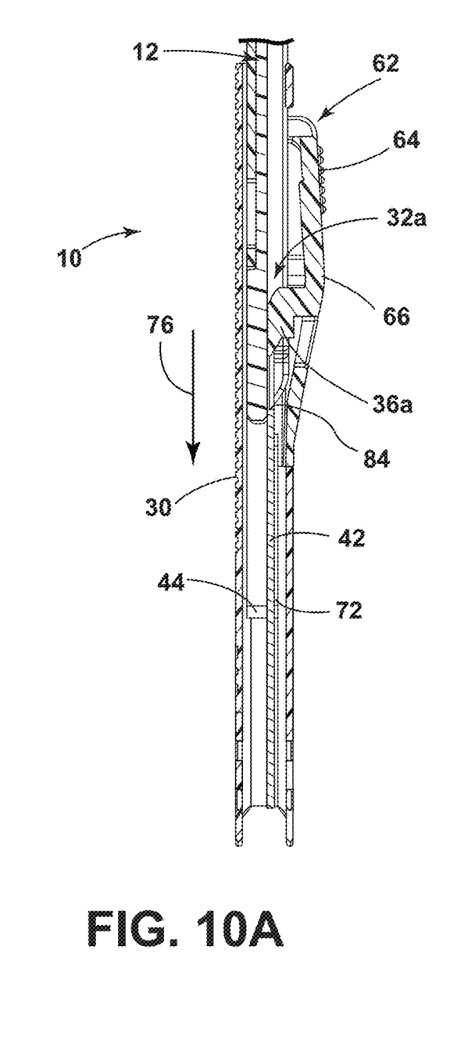
FIGS. 10A-10C are sequential cross-sectional views of the scalpel handle assembly during stages of movement of the shield into the removal position.
Figure 10B:
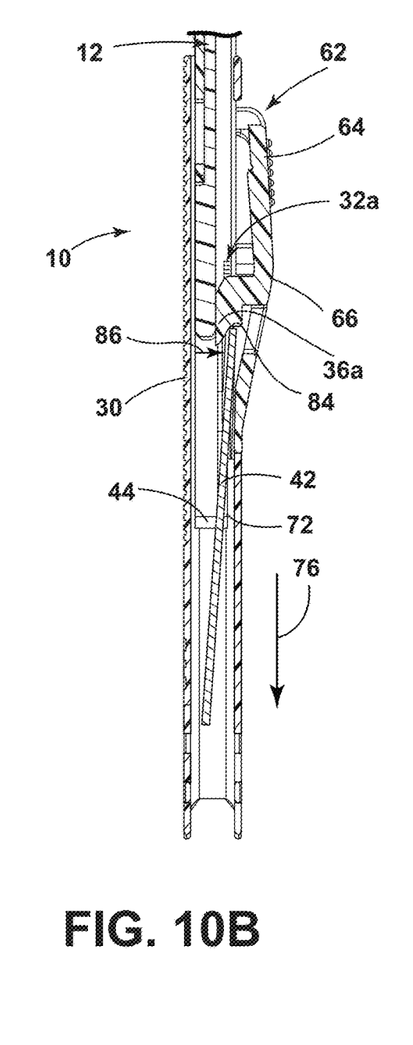
Figure 10C:
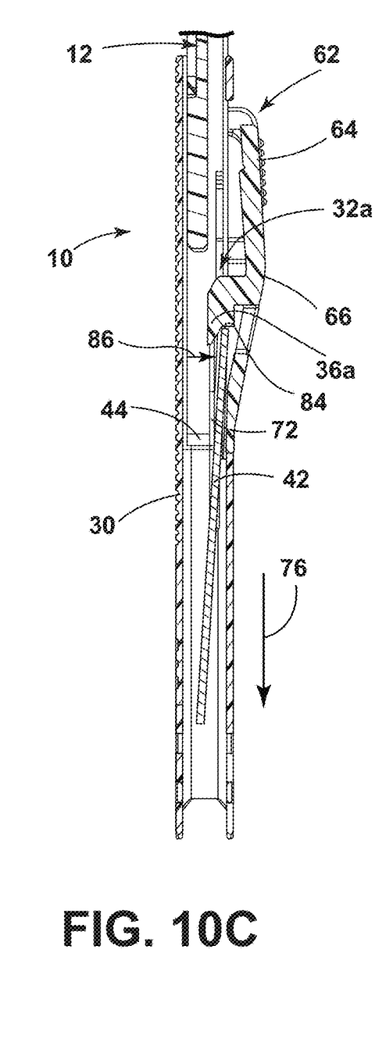
Figure 11:
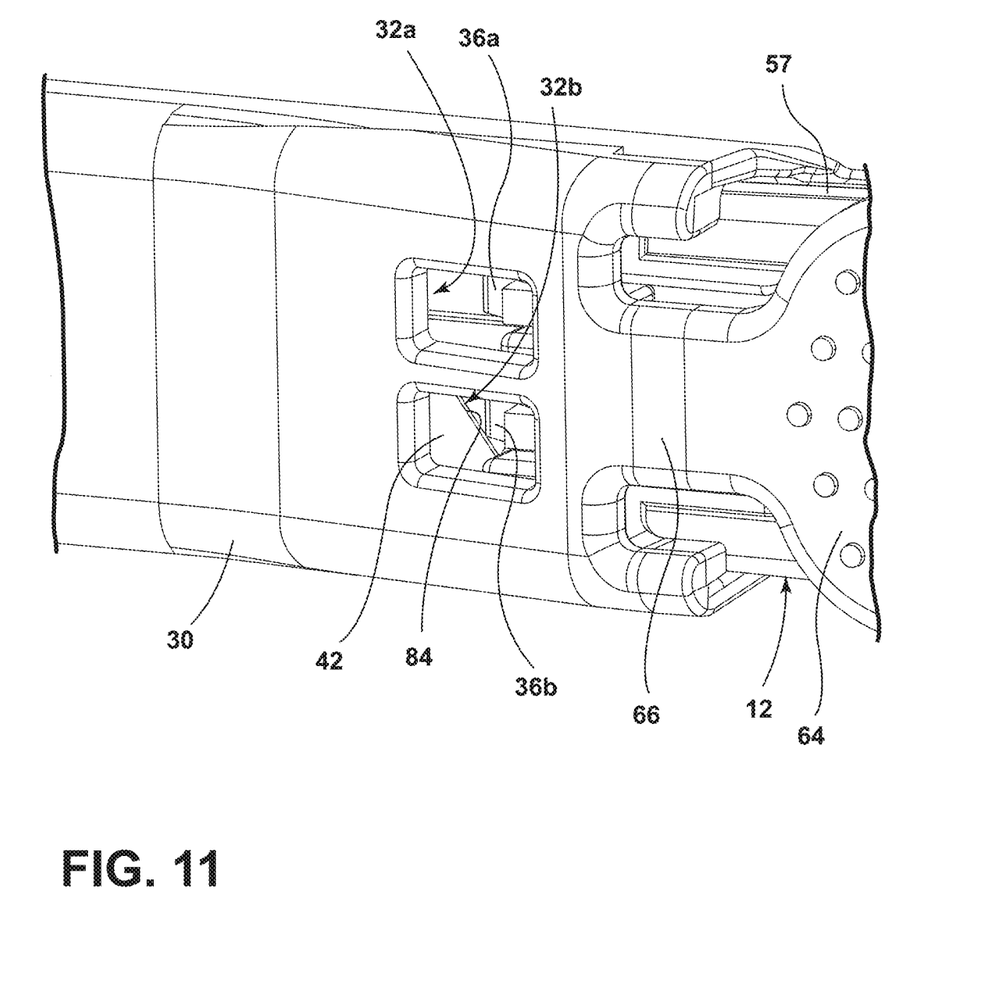
FIG. 11 is a detail view of a portion of the scalpel handle assembly of FIG. 1.

In particular, each removal flange 36a,36b, as depicted in FIGS. 10A, 10B, and 10C, is inclined at least along a portion thereof to define a removal wedge thereon that makes initial contact with trailing edge 84 of blade 42. By this configuration, the initial continued movement of shield 30 in direction 76 just after contact of at least one of the removal flanges 36a,36b with trailing edge 84 of blade 42 can move the trailing edge 84 outward with respect to tang 72, as shown in FIG. 10B. This can begin detachment of blade 42 from blade holder 44 such that continued movement of shield 30 in direction 76, as shown in FIG. 10C can cause trailing edge 84 of blade 42 to engage with a generally flat (i.e. perpendicular to direction 76) portion of removal flanges 36a,36b. This allows at least one of removal flanges 36a,36b to force blade 42 in direction 76 with movement of shield 30. When shield is moved fully into the removal position (FIG. 9), blade 42 is disengaged from blade holder 44 by sliding of slot 45 out of mounting slot 73, allowing blade 42 to fall out the open end of shield 30.

As shown in FIG. 8, secondary portion 78 of track 57 may be located inward of the adjacent portion of track 57 opposite first locking channel 54 therefrom. This can be such that shield 30 is prevented from being moved into the removal position (FIG. 9) except by depressing of button 64 beyond a position required for movement of shield 30 toward the retracted position. Such positioning of secondary portion 78 may also provide a positive stop for shield 30 when moved into the extended position, preventing premature blade 42 removal during normal use of handle 10. Secondary portion 78 is configured to require a predetermined amount of additional travel horizontally in direction 76 beyond the extended position to achieve blade removal. Further, the secondary portion 78 of track 57 is sloped back outward such that the outward biasing of locking mechanism 62 causes tabs 60 to urge shield 30 toward the removal position when engaged with secondary portion 78. It is further shown that an end 80 of track 57 is defined within secondary portion 78. The presence of end 80 may help ensure that the shield 30 does not accidentally become released from the body 12 during blade 42 removal.

After blade 42 removal, shield 30 can be moved back to either of the extended or retracted positions. A new blade 42 can be coupled with handle 10, as discussed above, while shield 30 is in the retracted position. If there is no intention to assemble a new blade 42 and if handle 10 is intended for single-use, it may then be disposed of.

As shown in FIG. 1, for example, body 12 of handle 10 can have an outwardly-flared rearward end 38 opposite first end 20. The outwardly-flared profile thereof can be such that the outer profile thereof generally matches that of shield 30 so that when shield 30 is in the illustrated retracted position, a generally consistent outer profile for handle 10 is achieved, which may provide increased comfort during use. Further, handle 10 may include a scale 40 imprinted or debossed thereon for use during a procedure or the like. The scale 40 may be continuous between flared portion 38 of body 12 and shield 30 and/or may extend along body for use when shield 30 is in the extended position (FIG. 8).

As shown in FIGS. 6 and 7, shield 30 may include one or more windows 82 therethrough so that a blade 42 assembled with handle 10 can be seen therethrough when shield 30 is in the illustrated extended position. In further examples shield 30 can additionally or alternatively be constructed of a transparent material.

Figure 12:
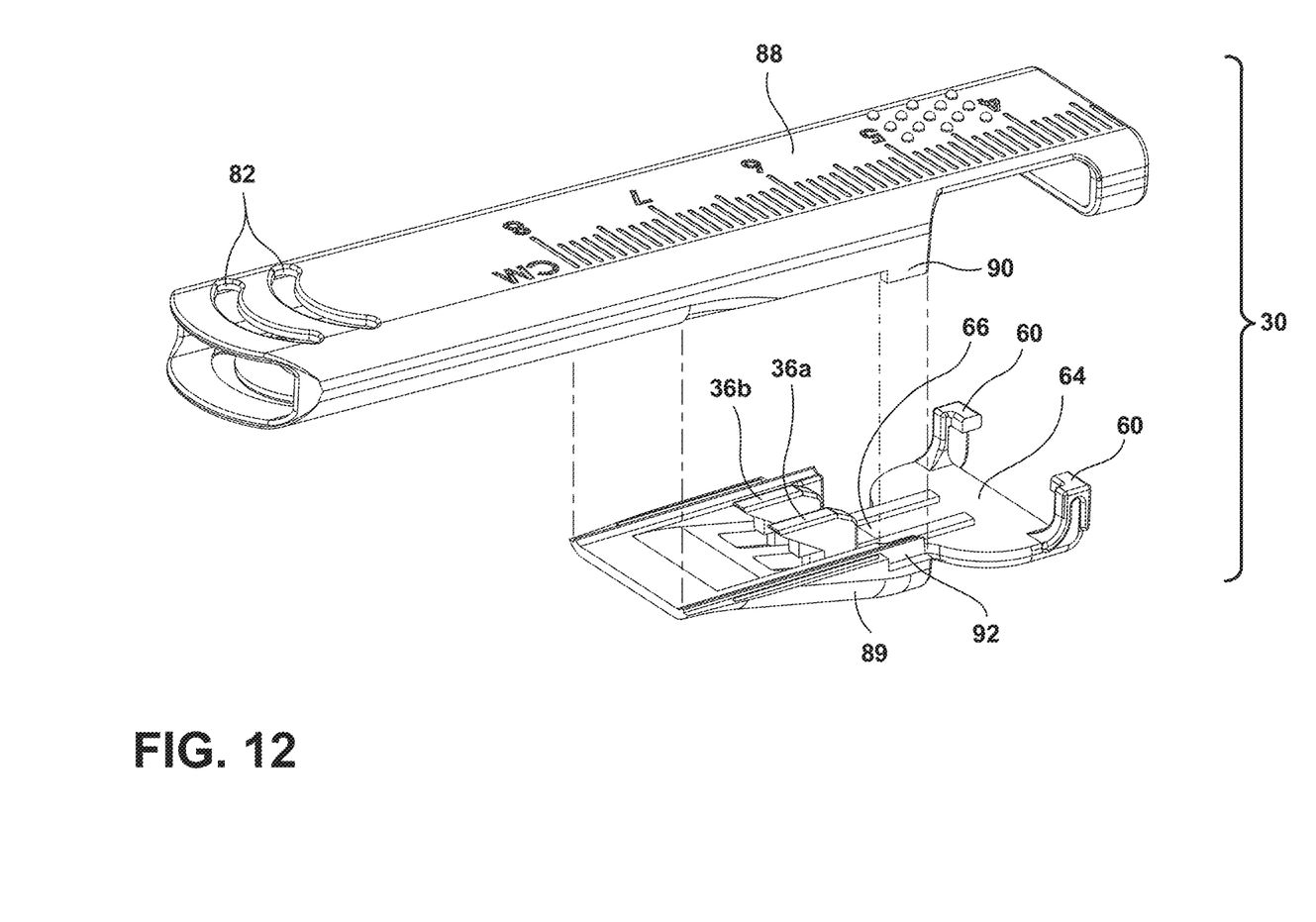
FIG. 12 is an exploded view showing an assembly of the shield.
Figure 13:
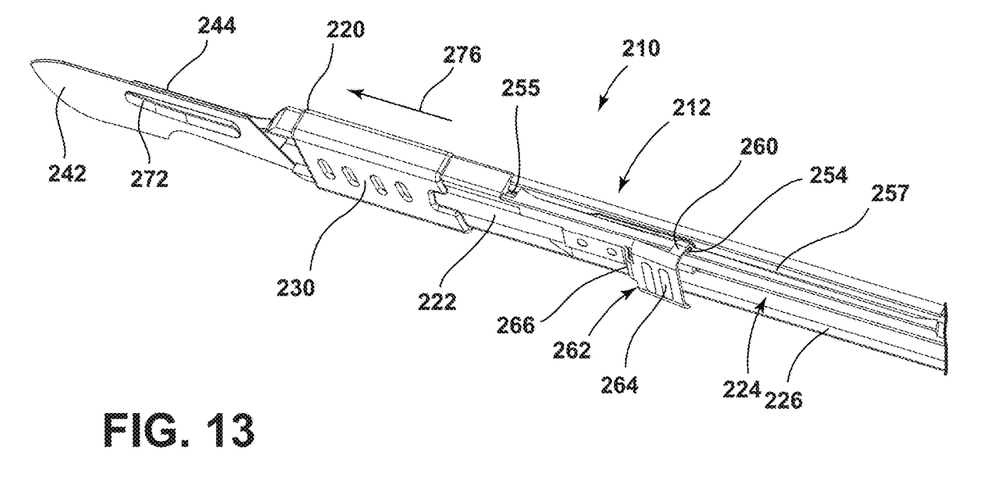
FIG. 13 is a rear perspective view of an alternative scalpel handle having a moveable insert in an extended position with respect to a body with an integrated shield, the handle assembled with a blade.

In one aspect, as illustrated in FIG. 12, shield 30 can be of a two-part plastic construction. In this construction, shield 30 can include a main portion 88 including the portion of shield 30 that surrounds body 12 and extends therefrom when in the extended position to conceal blade 42. A secondary portion 89 can include the button 64, tabs 60, and flexible portion 66 of the locking mechanism 62, discussed above. Secondary portion 89 can also include removal flanges 36a,36b, which can be configured to extend within main portion 88, as discussed above, when secondary portion 89 is assembled with main portion 88. Such construction can allow for an injection molded construction that includes removal flanges 36a,36b of a material thickness facilitating desired robustness of the removal flanges 36a, 36b, including along an interface thereof with the remaining portions of shield 30. Such material thickness may be difficult to achieve in a single piece shield 30, particularly without complicated molds and machinery. Secondary portion 89 can be rigidly coupled with main portion 88 such as by ultrasonic welding, laser welding, or the like, or with adhesives, for example. To aide in assembly of main portion 88 and secondary portion 89, main portion 88 may include an alignment tab 90 that may engage with a corresponding notch 92 in secondary portion 89.

Figure 14:
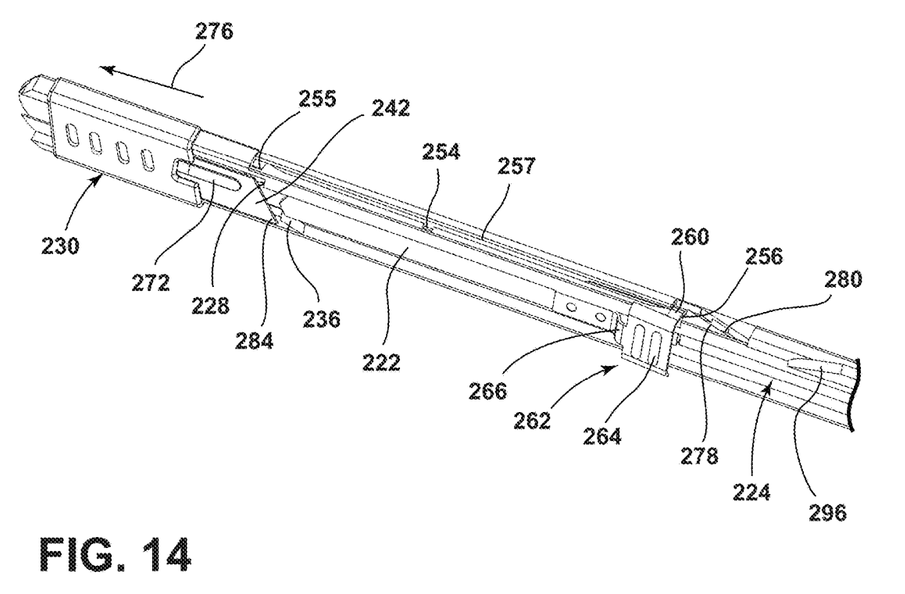
FIG. 14 is a rear perspective view of the alternative scalpel handle assembly of FIG. 13 with the moveable insert thereof in a retracted position with respect to the body.
Figure 15:
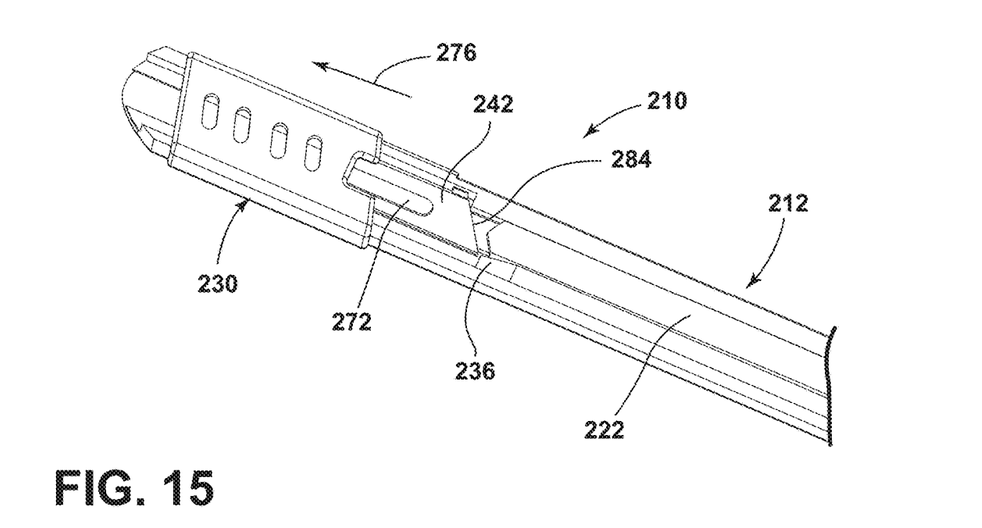
FIG. 15 is a bottom-rear perspective detail view of the alternative scalpel handle assembly of FIG. 13 with the moveable insert thereof moved toward a blade removal position with respect to the body.
Figure 16:
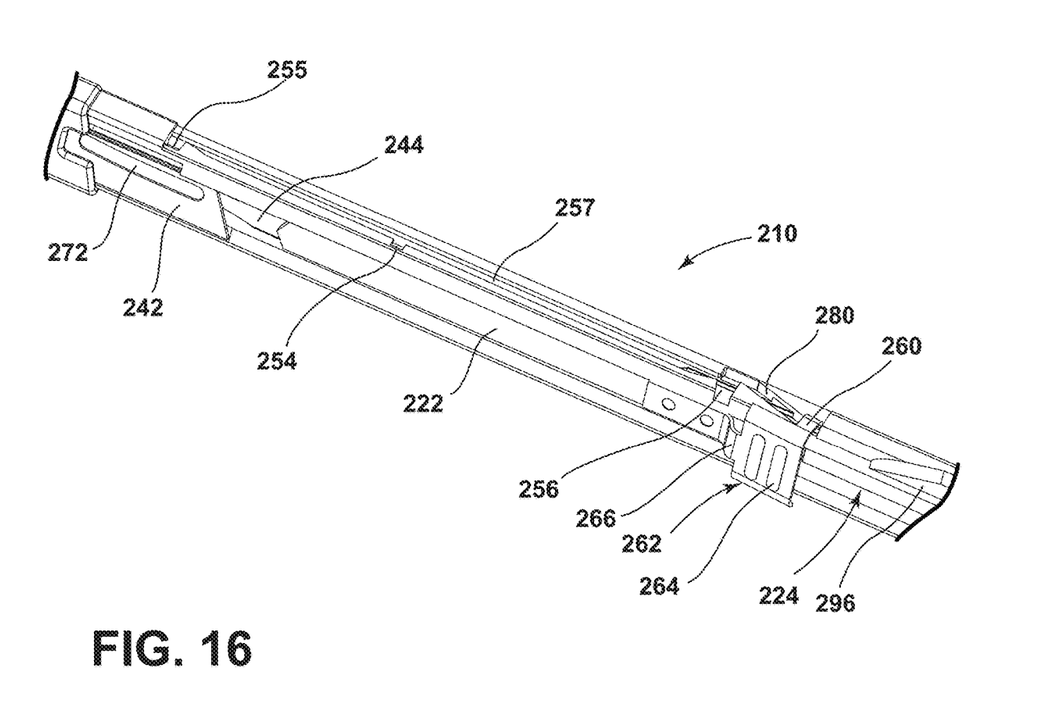
FIG. 16 is a rear perspective view of the alternative scalpel handle assembly of FIG. 13 with the moveable insert thereof in the blade removal position with respect to the body.

A further embodiment of a handle 210 is shown in FIGS. 13-16 that may be considered reusable. As such, both body 212 and insert 222 may be made of metal suitable for sterilization, such as using an autoclave or the like, such as stainless steel, various aluminum alloys, or the like. The variation of handle 210 illustrated in FIGS. 13-16 can include an integrated body 212 and shield 230 that are fixed together with shield 230 positioned adjacent end 220 of body 212. To retract blade within shield 230, handle 210 can include a moveable insert 222 that is slideably disposed within a cavity 224 in a side 226 of body 212. Insert 222 can be secured within cavity 224, for example, by one or more tabs 228, as illustrated in FIG. 14. In this variation, locking mechanism 262 can be coupled with insert 222 to allow for selective movement of insert 222 among various positions provided by track 257, similar to those discussed above. In particular, tab 260 of locking mechanism 262 can freely slide within track 257 between a locking channel 254 associated with an extended position, shown in FIG. 13, and an opposite locking channel 256 associated with a retracted position, shown in FIG. 14. It is noted that the more robust construction provided by the use of the above-mentioned metallic materials for insert 222, including button 260, and of body 212 may make it possible to incorporate only one track 257 on body 212. Accordingly, only a single tab 260 may be incorporated on button 264.

Although it may be possible to install blade 242 on blade holder 244 when insert 222 is in the extended position (FIG. 13), to further facilitate blade 242 installation, track 257 can further include a locking channel 255 associated with a blade installation, or fully-extended, position in which insert 222 is moved farther forward in direction 276 such that blade holder 244 can be accessed to install blade 242 thereon. Still further, an extension portion 280 of track 257 can be in communication with locking channel 256 such that, when button 264 is depressed by an amount sufficient to move tab 260 over ramp 278 (as shown in FIG. 14), insert 222 can be moved rearward such that trailing end 284 of blade 242 moves into contact with removal ramp 236 such that continued rearward movement of insert 222 causes blade 242 to become dislodged from blade holder 244.

To facilitate sterilization of handle 210 for subsequent reuse, button 264 can be pulled outwardly when insert 222 is in the retracted position (i.e. when tab 260 is in locking channel 256). This allows tab 260 to move out of locking channel 256, thereby allowing insert 222 to be moved further rearward (i.e. opposite direction 276) out of channel 224.

It will be understood by one having ordinary skill in the art that construction of the described device and other components is not limited to any specific material. Other exemplary embodiments of the device disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the device as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above is merely for illustrative purposes and not intended to limit the scope of the device, which is defined by the following claims as interpreted according to the principles of patent law, including the Doctrine of Equivalents.

What is claimed is:

1. A scalpel handle, comprising:
    a body defining a first end and a channel therein;
    a shield fixedly coupled with the body; and
    an insert defining a blade holder disposed at a first end thereof and slidably received within the channel of the body such that the blade holder is alternately positionable in an extended position disposed outwardly away from the first end of the body and a retracted position at least partially within the shield;
    wherein the body defines a removal wedge that is fixed with respect to the body and the shield and disposed in a substantially fixed lateral position at least partially aligned with a portion of the blade holder.

2. The scalpel handle of claim 1, wherein the channel is open on a first side of the body and extends in a longitudinal direction along the first side of the body.

3. The scalpel handle of claim 2, wherein the shield is disposed adjacent the first end of the body to enclose a portion of the channel.

4. The scalpel handle of claim 2, wherein the removal wedge is unitarily defined with the body and is disposed along a portion of the channel spaced from the shield at a distance less than a length of the blade holder.

5. The scalpel handle of claim 4, wherein the insert is slidably disposed within the channel of the body such that a portion of the blade holder passes the removal wedge during movement of the insert from the extended position past the retracted position and into a removal position wherein at least a portion of the blade holder is disposed on a side of the shield opposite the first end of the body.

6. The scalpel handle of claim 1, wherein the body further defines:
    a first locking channel; and
    a second locking channel spaced from the first locking channel by a distance equal to a distance traveled by the blade holder when moved from the extended position to the retracted position.

7. The scalpel handle of claim 6, wherein:
    the insert is slidably disposed within the channel of the body and further includes a button depressible toward the body, the button being alternately releasably engageable with the second locking channel to maintain the insert in the extended position and with the first locking channel to maintain the insert in the retracted position;

when engaged with the first locking channel or the second locking channel, the button is disengageable from the first locking channel and the second locking channel by movement thereof toward the body into a depressed position.

8. The scalpel handle of claim 7, wherein:
the blade holder is further positionable in an installation position wherein the blade holder is disposed outwardly from the first end of the body farther than when the blade holder is in the extended position; and
the body further defines a third locking channel spaced from the first locking channel by a distance equal to a distance traveled by the blade holder when moved from the extended position to the installation position.

9. The scalpel handle of claim 8, wherein the body further defines a guide track in communication with the first locking channel at a first end of the guide track to receive a portion of the button during movement of the insert out of the retracted position toward the extended position and in communication with the third locking channel at a second end of the locking channel to receive the portion of the button during movement of the insert out of the extended position and into the installation position.

10. A scalpel handle, comprising:
a body defining a channel extending in a longitudinal direction along a side thereof and having a shield portion disposed at a first end thereof that at least partially encloses the channel, a removal ramp defined monolithically with the body along a portion of the channel; and
an insert slidably disposed within the channel between a fully-extended position and a removal position with an intermediate extended position and a retracted position therebetween and having a blade holder defined on a first end thereof that passes the first end of the body during movement of the insert from the intermediate extended position to the retracted position and passes the removal ramp during movement of the insert into the removal position, wherein the removal ramp is spaced from the shield at a distance less than a length of the blade holder.

11. The scalpel handle of claim 10, wherein the channel is open on the side of the body.

12. The scalpel handle of claim 10, wherein the body further defines:
a first locking channel; and
a second locking channel spaced from the first locking channel by a distance equal to a distance traveled by the blade holder when moved from the intermediate extended position to the retracted position.

13. The scalpel handle of claim 12, wherein:
the insert further includes a button extending outwardly from the channel of the body and being depressible toward the body, the button being alternately releasably engageable with the second locking channel to maintain the insert in the intermediate extended position and with the first locking channel to maintain the insert in the retracted position;
when engaged with the first channel or the second channel, the button is disengageable from the first locking channel and the second locking channel by movement thereof toward the body into a depressed position.

14. The scalpel handle of claim 13, wherein the body further defines a third locking channel spaced from the second locking channel by a distance equal to a distance traveled by the blade holder when moved from the intermediate extended position to the fully-extended position, the button being further alternately releasably engageable with the third locking channel to maintain the insert in the fully extended position.

15. The scalpel handle of claim 14, wherein the body further defines a guide track in communication with the first locking channel at a first end of the guide track to receive a portion of the button during movement of the insert out of the retracted position toward the intermediate extended position and in communication with the third locking channel at a second end of the guide track to receive the portion of the button during movement of the insert out of the intermediate extended position and into the fully-extended position.

16. A scalpel handle, comprising:
a body defining a channel extending in a longitudinal direction along a side thereof and having a shield portion disposed at a first end thereof that at least partially encloses the channel, a removal ramp being fixedly defined along a portion of the channel; and
an insert:
having a blade holder defined on a first end thereof, the blade holder being configured for removably retaining a scalpel blade on the insert; and
slidably disposed within the channel between a retracted position and a removal position such that the blade holder, when retaining a scalpel blade thereon, moves from remote from the removal ramp to proximate the removal ramp, thereby bringing the scalpel blade into contact with the removal ramp and disengaging the scalpel blade from the blade holder, the removal ramp being spaced from the shield at a distance less than a length of the blade holder.

* * * * *